United States Patent [19]

Matsumura

[11] Patent Number: 4,867,554
[45] Date of Patent: Sep. 19, 1989

[54] SURFACE EXAMINING APPARATUS

[75] Inventor: Isao Matsumura, Yokosuka, Japan

[73] Assignee: Canon Kabushiki Kaisha, Tokyo, Japan

[21] Appl. No.: 146,702

[22] Filed: Jan. 21, 1988

[30] Foreign Application Priority Data

Jan. 26, 1987 [JP] Japan ............................. 62-15758

[51] Int. Cl.[4] ............................................ A61B 3/10
[52] U.S. Cl. ................................... 351/205; 351/206; 351/221
[58] Field of Search ............... 351/205, 206, 207, 208, 351/212, 221; 128/633; 354/62

[56] References Cited

U.S. PATENT DOCUMENTS 4,019,813  4/1977  Cornsweet et al. ................. 351/212
4,213,678  7/1980  Pomerantzeff et al. ........ 351/221 X

FOREIGN PATENT DOCUMENTS 52-123592  10/1977  Japan .
56-16103   2/1981   Japan .

Primary Examiner—Rodney B. Bovernick
Attorney, Agent, or Firm—Fitzpatrick, Cella, Harper & Scinto

[57] ABSTRACT

A surface examining apparatus in which a surface to be examined is scanned by a light, whereby scanning position information, depth information and reflected light amount information are obtained and at least the image of the surface to be examined is displayed on the basis of such information.

14 Claims, 2 Drawing Sheets

SURFACE EXAMINING APPARATUS

BACKGROUND OF THE INVENTION

1. Field of the Invention

This invention relates to a surface examining apparatus capable of examining a surface including depth information, for example, a surface examining apparatus which can be used for ophthalmic examination such as the examination of glaucoma.

2. Related Background Art

In the heretofore known ophthalmic examining apparatus, an eye fundus camera has been widely used as the means for recording information of an eye to be examined, for example, the information of the eye fundus. To gather the uneven state of the eye fundus, there have been practiced a method simply stereo-photographing the eye fundus and gathering the uneven state of the eye fundus from the image of the eye fundus and a method of projecting a striped pattern onto the eye fundus and gathering the uneven state of the eye fundus from the shape of the image of the striped pattern. However, in the former method, it is difficult to transform the depth of the unevenness into the form of a numerical value. In the latter method, it is necessary to accurately superpose and project a striped pattern. In a case where, for example, the state of the depth profile of an optic disc, which is information for judgment of glaucoma is to be examined, the depth profile is wiped out by an illuminating light for the observation of the eye fundus image. This leads to the disadvantage that measurement becomes impossible or discontinuity occurs due to the measurement conforming to the interval between the stripes.

In the field of eye fundus cameras U.S. Pat. No. 4,213,678 discloses a known technique of scanning and illuminating the eye fundus by a light, but this patent only discloses the detection of the eye fundus image and does not disclose the detection of the depth distribution information of the eye fundus.

Also, in Japanese Laid-Open Patent Application No. 16103/1981, there is disclosed as an eye refractometer, the technique of projecting a predetermined index mark onto a predetermined portion of the eye fundus, providing light beam separating means in the optical path for receiving the reflected light from the eye funduds, and finding the refractive power of the eye from the position of the image of the index mark onlight position detecting means. However, this publication of course does not disclose the technical idea of detecting the depth distribution informaiton of the eye fundus. Further, an eye refractometer and an eye fundus camera differ fundamentally from each other, and this disclosure simply cannot be combined with U.S. Pat. No. 4,213,678.

SUMMARY OF THE INVENTION

It is an object of the present inventin to provide a surface examining apparatus which is capable of quantitatively detecting the depth distribution information of a surface to be examined.

It is a further object of the present invention to provide a surface examining apparatus which is capable of displaying the corrected image of a surface to be examined on the basis of the depth distribution informaiton of the surface to be examined.

DESCRIPTION OF THE PREFERRED EMBODIMENTS

The present invention will hereinafter be described in detail with respect to an embodiment applied to an ophthalmic examining apparatus.

Figure 1:
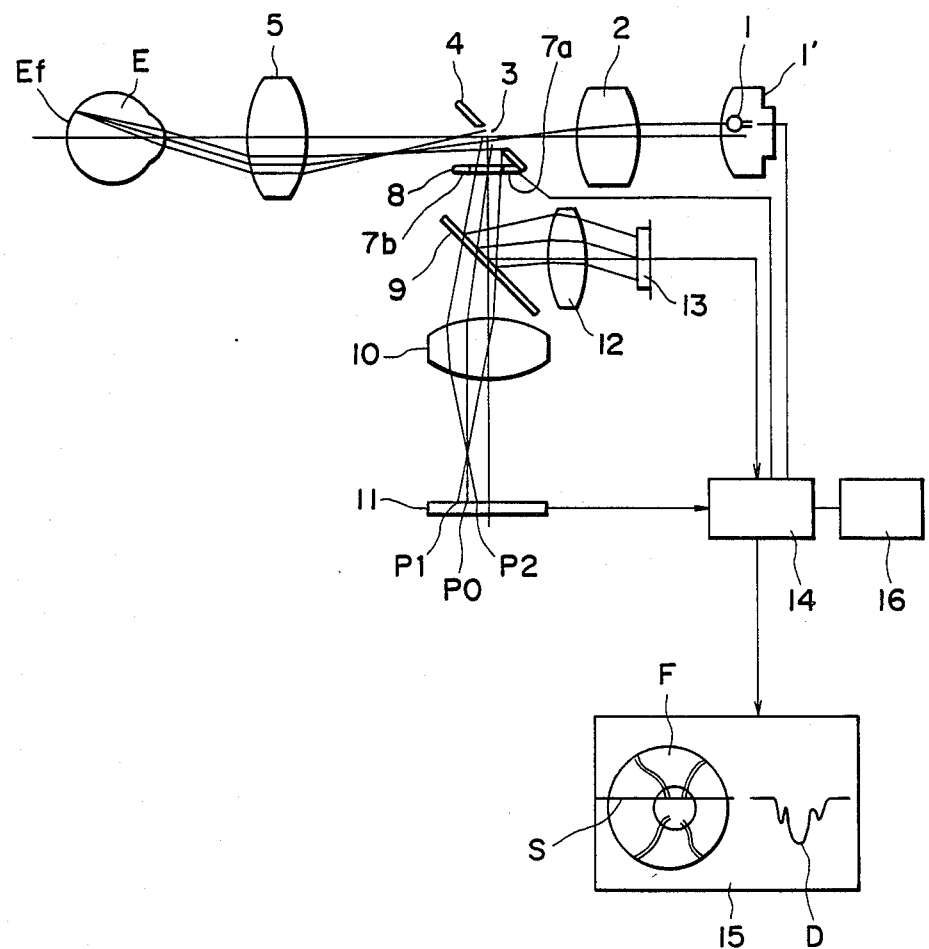
FIG. 1 shows the general construction of an embodiment of the present invention.

Referring to FIG. 1, reference numeral 1 designates a point source of light comprising a coalescence point, for example, a scanning light source on the lightemitting surface of a cathode ray tube scanner 1'. The scanning light source may be one provided by scanning of a polygon mirror or the like. On an optic axis passing through the point source of light 1 and an eye E to be examined, there are disposed, in succession from the point source of light 1 side, a projection lens 2, an apertured mirror 4 having an aperture stop 3 at the center thereof and provided obliquely, and an objective lens 5. On the reflection side of the apertured mirror 4 which reflects the light beam from the objective lens 5, there are disposed a light-receiving stop 8 comprising a combination of a liquid crystal plate block 6 shown in FIG. 2 and a light-receiving mask 7 having two stop apertures 7a and 7b also shown in FIG. 2, a beam splitter 9, a projection lens 10, and a planar image pick-up element 11 comprising a two-dimensional solid state image pick-up element which is a light position detecting sensor substantially conjugate with the eye fundus Ef, such as a two-dimensional CCD. Also, in the direction of reflection of the beam splitter 9, there are provided a projection lens 12 and a light-receiving element 13 which serves as a light amount detecting sensor disposed at a position substantially conjugate with the pupil of the eye E to be examined. The outputs of the planar image pick-up element 11 and the light-receiving element 13 are connected to an electrical processing unit 14, the output of which is connected to the point source of light 1, the liquid crystal plate block 6 and image display means 15 comprising a Braun tube or the like.

The light beam from the point source of light 1 passes through the projection lens 2, the aperture stop 3 disposed near the aperture in the apertured mirror 4 and the objective lens 5 to the interior of the eye E to be examined, and irradiates a point on the eye fundus Ef. The light reflected by the eye fundus Ef passes through the objective lens 5 again and is reflected by the mirror portion of the apertured mirror 4, whereafter it passes through the light-receiving stop 8 comprising a combination of the liquid crystal plate block 6 and the light-receiving mask 7 as shown in FIG. 2 and further through the beam splitter 9 and is projected onto the planar image pick-up element 11 by the projection lens 10.

Figure 2:
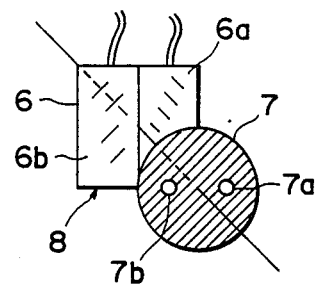
FIG. 2 is a perspective view of a light-receiving stop.

The aforementioned light-receiving stop 8 is for taking out depth information, and is comprised of a combination of the light-receiving mask 7 having two stop apertures 7a and 7b provided point-symmetrically with respect to the optic axis as shown, for example, in FIG. 2 and the liquid crystal plate block 6 comprising two liquid crystal plates 6a and 6b independently covering the step apertures 7a and 7b, respectively, and is adapted to alternately shield the stop apertures 7a and 7b from the light by means of the two liquid crystal plates 6a and 6b. Accordingly, if it is out of focus, the light beam projected onto the planar image pick-up element 11 becomes light spots in which the lights passing through the stop apertures 7a and 7b (which are the pupils of the light-receiving optical system) are separated from eachother as indicated by P1 and P2 as shown in FIG. 1 and if it is in focus, the light beam becomes a single light spot in which the light spots are coincident with each other as indicated by P0. Further, depending on whether the focal plane lies before or behind the planar image pick-up element 11, the coordinates of the light spots alternately projected are replaced with each other and thus, it becomes possible to gather that information as well.

Figure 3:
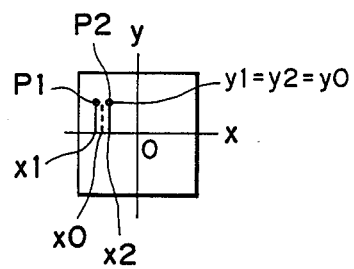
FIG. 3 illustrates the positions of light spots projected onto a planar image pick-up element.

FIG. 3 shows this state, and represents the positions of the light spots on the x, y coordinates. THe coordinates of the two light spots P1 and P2 are (x1, y1) and (x2, y2), respectively (where y1=y2=y0), and the coordinates of the centers thereof are detectable as (x0, y0). From this, the light spot on the eye fundus Ef has the coordinates (x0, y0) on the planar image pick-up element 11, and the depth $\Delta$ thereof can be calculated as a value proportional to (x1−x2). By plotting $\Delta$ at each scanning position, the depth distribution can be grasped. When the number of the stop apertures is not two but one, the depth $\Delta$ can likewise be calculated by finding the absolute position of a single light beam or the planar image pick-up element 11. On the other hand, as regards the image information, measurement is effected with the reflected light beam from the eye fundus Ef being separated, and for this purpose, the light beam reflected by the apertured mirror 4 and passed through the light-receiving stop 8 is divided by the beam splitter 9 and the divided light beams are projected onto the light-receiving element 13 by the projection lens 12. In this case, the light-receiving stop 8 is so disposed as to be imaged on the light-receiving element 13, and since the size of the pupil will not vary, this is convenient for measurement. The concentration of the light sopot on the coordinates (x0, y0) can be determined by the output signal of the light-receiving element 13 and therefore, if the point source of light 1 is scanned in the area of the eye fundus Ef, the map of the eye fundus surface and the information in the direction of depth thereof will be obtained. The information of the light-receiving element 13 and the information of the planar image pick-up element 11 are displayed on the image display means 15 via the electrical processing unit 14.

Figure 4:
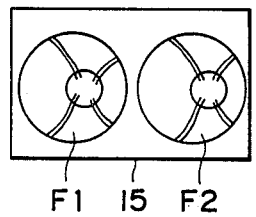
FIG. 4 illustrates stereo images.

With respect to the forms of the images displayed on the image display means 15, the eye fundus image F and the depression figure D on any cross-section S are conceivable as shown, for example, in FIG. 1, and in this case, the designation of the cross-section can be selected arbitrarily by inputting it from a terminal 16 to a microprocessor and the depth information can be displayed as by a horizontal line together with that portion of the image information it corresponds to. As a further display method, it is also conceivable to depict the eye fundus image and a contour figure superposed thereon or a monochromatic or colored concentration figure corresponding to the depression. Also, by using the liquid crystal shutters 6a and 6b alternately, respective eye fundus images F1 and F2 can be depicted side by side on the same screen of the image display means 15 in conformity with the light beams passing through the two stop apertures 7a and 7b substantially outside the axis, as shown in FIG. 4, and stereoscopic observation will also become possible of the observing these images by left and right eyes, respectively.

Figure 5:
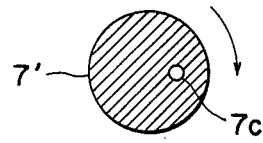
FIG. 5 shows a modification of a light-receiving mask.

In the above-described embodiment, the stop apertures 7a and 7b have been shown as being fixedly provided, but alternatively, as shown in FIG. 5, a light-receiving mask 7' having a single off-axis stop aperture 7c may be rotated about the optic axis and the light spot image may be measured at two points symmetric with the optic axis.

Further, besides the above-described embodiment, it is of course possible to make the forms of the projection side and the light-receiving side converse, that is, to make the position of the aperture stop converse so as to pass the light beam through the off-axis aperture during projection and pass the light beam through the central aperture during light reception.

Also, as regards the coordinates P0 of the image, it is possible to determine it by the coordinates on the projection side, i.e., at the scanning position of the cathode ray tube scanner 1', instead of determining it on the image receiving side, i.e., at the light beam position on the planar image pick-up element 11.

Also, in the foregoing description, discrete light-receiving means have been used for the determination of the XY coordinates of the image and the determination of the concentration, but the concentrationcan also be determined directly from the output of the planar image pick-up element.

Now, if there is a difference in the depth when the concentration is measured at the received light amount level, even if the reflected light is one from the same point on the eye fundus, the light-receiving level varies and therefore, in roder to eliminate this, it is desirable that the received light amount level be corrected on the basis of the depth information. This may be accomplished as by setting a complete diffusing surface as the surface to be examined, defining the light amount level when the spacing between P1 and P2 is zero as a reference light amount level, causing the microprocessor 14 to memorize the light amount level when the complete diffusing surface has been shifted by a predetermined amount in the direction of the optic axis and preparing a correction coefficient in advance.

Figure 6:
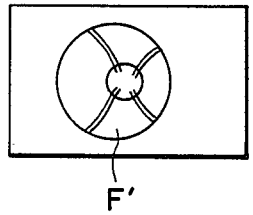
FIG. 6 shows the image of a surface to be examined corrected on the basis of the depth distribution information of the surface to be examined.

Further, in order to prevent the width ofthe scanning light beam on the planar image pick-up element 11 from being varied by the depth position to thereby cause defocus, the spacing between P1 and P2 when the complete diffusing surface has been shifted by a predetermined amount in the direction of the optic axis with the state in which the spacing between P1 and P2 is approximately zero as the reference can also be memorized by the microprocessor 14. In this case, when the eye fundus surface which is actually an uneven surface to be examined is to be imaged, the uneven portion is defocused, but the uneven portion can be electrically eliminated and the corrected image as a flat sharp eye fundus surface is possible. Thus, in this case, the blurred depression in the eye fundus image F in FIG. 1 is displayed as a blurfree corrected eye fundus image F' (FIG. 6).

As described above, according to the present invention, the depth information can be obtained and thus, it becomes possible, for example, to display as an image the degree of depression, i.e., the C/D ratio, of the optic disc which plays an important role in the judgment of glaucoma, and to precisely measure the area portion thereof, and accuracy can be brought about particularly in the diagnosis of glaucoma.

While the embodiment of the present invention has been described withrespect to an ophthalmic examining apparatus, the present invention is also applicable to other medical examining apparatus or industrial examinations.

I claim:

1. An eye surface examining apparatus comprising:
   a light source for scanning the eye surface to be examined through a lght projection portion of an anterior part of the eye to be examined;
   a light-receiving optical sysstem for receiving reflected light from the eye surface to be examined, said light receiving optical system having a stop provided with a lighttransmitting portion for transmitting the reflected light from the eye surface therethrough, said stop being disposed at a position in a plane substantially conjugate with the anterior part of the eye, a portion corresponding to said light transmitting portion in the anterior part of the eye being disposed at a position different from said light projection portion;
   light position detecting means provided substantially with the eye surface to be examined with respect to said light-receiving optical system for detecting information concerning the depth of the surface to be examined at each scanning position on the basis of a position of incidence of the scanning light reflected from the eye surface to be examined by way of said stop;
   scanning position detecting means for detecting each scanning position on the eye surface to be examined;
   light amount detecting means for detecting the scanning light amount reflected from each scanning position in the surface to be examined; and
   image display means for displaying at least the image of the eye surface to be examined on the basis of the outputs of said light position detecting means, said scanning position detecting means, said light amount detecting means.

2. An eye surface examining apparatus according to claim 1, wherein said light amount detecting means is substantially conjugate with the pupil of the eye to be examined.

3. An eye surface examining apparatus according to claim 1, wherein said light position detecting means is a two-dimensional solid state image pick-up element.

4. An eye surface examining apparatus according to claim 1, wherein said light position detecting means serves also as said light amount detecting means.

5. An eye surface examining apparatus according to claim 1, wherein said light position detecting means serves also as said scanning position detecting means.

6. An eye surface examining apparatus according to claim 1, wherein said image display means displays the image of the eye surface to be examined and the depth distribution of the eye surface to be examined.

7. An eye surface examining apparatus according to claim 6, wherein said image display means further displays that portion of the eye surface to be examined that said depth distribution corresponds to.

8. An eye surface examining apparatus according to claim 1, wherein said image display means displays the image of the eye surface to be examined corrected on the basis of the depth distribution of the eye surface to be examined.

9. An eye surface examining apparatus according to claim 1, wherein said stop has two lighttransmitting portions.

10. An eye surface examining apparatus according to claim 9, wheein said image display means displays two images o the surface to be examined for stereoscopic observation by the use of light beams passed through the respective light-transmitting portions.

11. An eye surface examining apparatus according to claim 1, wherein said stop is rotatable about the optic axis.

12. An eye surface examining apparatus according to claim 1, wherein said light source scanning means is a cathode ray tube scanner.

13. An eye surface examining apparatus according to claim 1, wherein the surface to be examined is an eye fundus surface.

14. An eye surface examining apparatus comprising;
   a light source for scanning the eye surface to be examined through a light projection portion of an anterior part of the eye to be examined;
   a light-receiving optical system for receiving reflected light from the eye surface to be examined, said light receiving optical system having a stop provided with a light-transmitting portion for transmitting the reflected light from the eye surface therethrough, said stop being disposed at a position in a plane substantially conjugate with the anterior part of the eye, a portion corresponding to said light transmitting portion in the anterior part of the eye being disposed at a position different from said light projection portion;
   light position detecting means provided substantially conjugate with the eye surface to be examined with respect to said light-receiving optical system for detecting information concerning the depth of the surface to be examined at each scanning position on the basis of a position of incidence of the scanning light by way of said stop reflected from the eye surface to be examined;
   scanning position detecting means for detecting each scanning position on the eye surface to be examined; and
   light amount detecting means for detecting the scanning light amount reflected from each scanning position in the surface to be examined.

* * * * *

UNITED STATES PATENT AND TRADEMARK OFFICE
CERTIFICATE OF CORRECTION

PATENT NO. : 4,867,554
DATED : September 19, 1989
INVENTOR(S) : Isao Matsumura It is certified that error appears in the above-identified patent and that said Letters Patent is hereby corrected as shown below:

COLUMN 1
  Line 17, change "method" to --method of--.
  Line 23, change "ofthe" to --of the--.
  Line 29, change "glaucoma" to --glaucoma,--.
  Line 47, change "eye funduds," to --eye fundus,--.
  Line 49, change "onlight" to --on light--.
  Line 52, change "informaiton" to --information--.
  Line 60, change "inventin" to --invention--.
  Line 67, change "informaiton" to --information--.

COLUMN 2
  Line 22, change "lightemitting" to --light-emitting--.
  Line 38, change "solid state" to --solid-state--.

COLUMN 3
  Line 6, change "step apertures 7a and 7b," to --stop apertures 7a and 7b,--.
  Line 11, change "lights" to --light--.
  Line 14, change "eachother" to --each other--.
  Line 15, change "FIG. 1" to --FIG. 1,--.

UNITED STATES PATENT AND TRADEMARK OFFICE
CERTIFICATE OF CORRECTION

PATENT NO. : 4,867,554
DATED : September 19, 1989
INVENTOR(S) : Isao Matsumura

It is certified that error appears in the above-identified patent and that said Letters Patent is hereby corrected as shown below:

COLUMN 3 (Continued)
    Line 32, change "grasped" to --determined--.
    Line 35, change "or" to --on--.
    Line 47, change "light sopot" to --light spot--.

COLUMN 4
    Line 8, change "of the" to --by--.
    Line 9, change "by" to --of the--.
    Line 33, change "concentrationcan" to --concentration can--.
    Line 40, change "roder" to --order--.
    Line 51, change "ofthe" to --of the--.
    Line 63, change "image" to --imaging--.
    Line 66, change "blurfree" to --blur-free--.

UNITED STATES PATENT AND TRADEMARK OFFICE
CERTIFICATE OF CORRECTION

PATENT NO. : 4,867,554
DATED : September 19, 1989
INVENTOR(S) : Isao Matsumura It is certified that error appears in the above-identified patent and that said Letters Patent is hereby corrected as shown below:

COLUMN 5
    Line 8, change "withrespect" to --with respect--.
    Line 17, change "sysstem" to --system--.
    Line 20, change "lighttransmitting" to --light-transmitting--.
    Line 25, change "light transmitting to --light-transmitting--.
    Line 28, change "substantially" to --substantially conjugate--.
    Line 46, change "means, said" to --means, and said--.
    Line 54, change "solid state" to --solid-state--.

COLUMN 6
    Line 15, change "lighttransmitting" to --light-transmitting--.
    Line 18, change "wheein" to --wherein--.
    Line 19, change "o" to --of--.
    Line 31, change "comprising;" to --comprising:--.
    Line 37, change "light receiving" to --light-receiving--.
    Line 43, change "light transmitting" to --light-transmitting--.

UNITED STATES PATENT AND TRADEMARK OFFICE
CERTIFICATE OF CORRECTION

PATENT NO. : 4,867,554

DATED : September 19, 1989

INVENTOR(S) : Isao Matsumura

It is certified that error appears in the above-identified patent and that said Letters Patent is hereby corrected as shown below:

COLUMN 6 (Continued)

Line 43, change "light transmitting" to --light-transmitting--.

Signed and Sealed this

Thirtieth Day of June, 1992

Attest:

DOUGLAS B. COMER

Attesting Officer

Acting Commissioner of Patents and Trademarks